(12) United States Patent
Hannes (10) Patent No.: US 10,888,250 B2
(45) Date of Patent: Jan. 12, 2021

(54) SYSTEM AND DEVICE FOR MEASURING THE RATE OF FLOW OF AN EXHALED OR INHALED AIRFLOW

(71) Applicant: FIM MEDICAL, Villeurbanne (FR)

(72) Inventor: Benjamin Hannes, Chaponost (FR)

(73) Assignee: FIM MEDICAL, Villeurbanne (FR)

( * ) Notice: Subject to any disclaimer, the term of this patent is extended or adjusted under 35 U.S.C. 154(b) by 7 days.

(21) Appl. No.: 14/784,191

(22) PCT Filed: Mar. 26, 2014

(86) PCT No.: PCT/FR2014/050718
§ 371 (c)(1),
(2) Date: Oct. 13, 2015

(87) PCT Pub. No.: WO2014/177781
PCT Pub. Date: Nov. 6, 2014

(65) Prior Publication Data
US 2016/0066817 A1    Mar. 10, 2016

(30) Foreign Application Priority Data

Apr. 30, 2013  (FR) ...................................... 13 53974

(51) Int. Cl.
| | |
|---|---|
| *A61B 5/097* | (2006.01) |
| *A61B 5/087* | (2006.01) |
| *B29C 45/00* | (2006.01) |
| *B29L 31/00* | (2006.01) |

(52) U.S. Cl.
CPC .............. *A61B 5/097* (2013.01); *A61B 5/087* (2013.01); *B29C 45/00* (2013.01); *A61B 2562/12* (2013.01); *B29L 2031/753* (2013.01)

(58) Field of Classification Search
None
See application file for complete search history.

(56) References Cited

U.S. PATENT DOCUMENTS

| | | | |
|---|---|---|---|
| 6,354,115 B1 * | 3/2002 | Zahn ....................... | D06F 37/00 68/133 |
| 2002/0029003 A1 | 3/2002 | Mace et al. | |
| 2006/0147141 A1 * | 7/2006 | Harwood ................ | F16C 33/80 384/480 |

FOREIGN PATENT DOCUMENTS

FR          2016180 A1 *   5/1970   ............. A61B 5/087

OTHER PUBLICATIONS

International Search Report dated Jun. 25, 2014 re: Application No. PCT/FR2014/050718; pp. 1-2.

* cited by examiner

*Primary Examiner* — Kaylee R Wilson
*Assistant Examiner* — Jay B Shah
(74) *Attorney, Agent, or Firm* — Cantor Colburn LLP (57) ABSTRACT

A system for measuring the flow rate of an airflow exhaled or inhaled by a person includes a measuring apparatus and a device. The device includes a tubular pipe for guiding the airflow and a structure with a plurality of ducts configured to separate the airflow. The device further includes a first groove opening into the outer face of the wall of the tubular pipe and a component for communicating fluidically with at least one peripheral duct in the structure. A second groove, distanced from the first groove, opens into the outer face of the wall of the tubular pipe and includes a component for communicating fluidically with the at least one peripheral duct.

10 Claims, 6 Drawing Sheets

SYSTEM AND DEVICE FOR MEASURING THE RATE OF FLOW OF AN EXHALED OR INHALED AIRFLOW

FIELD

The disclosure relates to a device and a system for measuring a flow rate of an air flow exhaled or inhaled by a person, as well as a method for manufacturing the device.

BACKGROUND

It is known to use a pneumotachograph for measuring a flow rate of an air flow exhaled or inhaled by a person. The pneumotachograph comprises a tubular conduit through which the person exhales or inhales.

The tubular conduit is provided with an inner structure intended to create a pressure drop by partially obstructing the tubular conduit.

The pneumotachograph also comprises a pressure measuring apparatus connected to the tubular conduit for measuring a differential pressure on either side of the structure or at two distant locations of the structure along the flowing direction of the flow.

The sensor is a Fleisch pneumotachograph wherein the structure presents a plurality of capillaries parallel to the flowing direction. When passing through the structure, the air flow is split into a plurality of Poiseuille flows, each flow passing through one capillary.

It is known to measure a differential pressure between two distant locations of the same capillary. The distance between the two locations and the nature of the Poiseuille flow allow deducing the flow rate of the air flow.

It is known to have a structure realized from a serrated stainless steel strip superimposed on a flat strip. The serrated strip and the flat strip are rolled so as to create the structure comprising a plurality of capillaries.

This arrangement is satisfactory in that the structure presents a plurality of capillaries parallel to the flowing direction of the air flow allowing to separate the flow into a plurality of Poiseuille flows.

Nonetheless, the method for obtaining the structure from a serrated strip and a flat strip is complex to implement. The geometric tolerances of the dimensions of the capillaries have to be met. The dimensional disparities have an effect on the measured differential pressure and are likely to lead to a measurement error, that is why this type of devices requires calibration.

In addition, the manufacturing cost requires the use of the same device for several persons, which can create a risk of microbial contamination from one person to another if the usage and decontamination procedures are not properly followed.

The present disclosure aims to resolve all or part of the aforementioned drawbacks.

SUMMARY

To this end, the present disclosure concerns a device for measuring a flow rate of an air flow exhaled or inhaled by a person, comprising a tubular conduit provided for conducting said air flow, the tubular conduit comprising a wall presenting an inner face and an outer face. The device further comprises a structure disposed in the tubular conduit and comprising a plurality of channels intended for dividing the air flow.

The device presents a first groove opening onto the outer face of the wall of the tubular conduit and being in fluid communication with at least one peripheral channel of the structure.

The device also presents a second groove opening onto the outer face of the wall of the tubular conduit and being in fluid communication with said at least one peripheral channel.

The second groove is arranged at a distance from the first groove.

The plurality of channels imposes a pressure drop on the flow passing through the structure. The first and second grooves are openings arranged for measuring a differential pressure at two distant locations of the structure along the flowing direction of the air flow.

The measurement of the differential pressure, combined with the knowledge of the geometry of the channels, allows deducing the flow rate of the air flow passing through the tubular conduit.

Preferably, the plurality of channels is dimensioned so as to divide the air flow into a plurality of Poiseuille flows.

The device according to the disclosure constitutes a single-use element which may in particular be realized into one single-piece by injection. The benefit of realizing the device into one single-piece by injection is to obtain a part with strictly identical dimensional aspects. Hence, the devices are interchangeable and the system no longer requires calibration.

According to one aspect of the disclosure, the first groove is in fluid communication with a plurality of peripheral channels of the structure, and the second groove is in fluid communication with said plurality of peripheral channels of the structure.

The benefit of performing the differential pressure measurement on a plurality of channels is to increase the accuracy of the measurement. Indeed, the measured differential pressure is the mean of the differential pressures of the plurality of peripheral channels.

According to one aspect of the disclosure, the channels of the plurality of peripheral channels present identical dimensions.

Preferably, the plurality of peripheral channels of the structure is constituted by the set of channels that are located at the periphery of the structure.

According to one aspect of the disclosure, the first groove extends along a first circumference of the outer face of the tubular conduit and the second groove extends along a second circumference of the tubular conduit.

According to one aspect of the disclosure, the tubular conduit and the structure are integral with each other.

According to one aspect of the disclosure, the structure extends over the section of the tubular conduit.

The tubular conduit comprises a first free portion and a second free portion disposed on either side of the structure.

According to one aspect of the disclosure, the first and the second grooves are distant from the ends of the peripheral channels.

Thus, the flows in the channels are established between the first and the second grooves. Thus, each flow presents, over the sections between the first and the second grooves, a constant transverse profile of flow velocities with a non-turbulent flow regime.

According to one aspect of the disclosure, the tubular conduit is a revolving conduit, the axis of revolution being coincident with the direction of extension of the tubular conduit.

According to one aspect of the disclosure, the first circumference is comprised in a first plane orthogonal to the axis of revolution and in which the second circumference is comprised in a second plane orthogonal to the axis of revolution.

According to one aspect of the disclosure, the channels present identical sections in every plane orthogonal to the axis of revolution between the ends of the channels.

According to one aspect of the disclosure, the channels are evenly distributed around a central channel.

According to one aspect of the disclosure, the tubular conduit is a straight tube.

According to one aspect of the disclosure, the diameter of the inner face of the tubular conduit is constant.

According to one aspect of the disclosure, the device comprises a tubular mouthpiece.

The mouthpiece is intended to be positioned, in part, in the mouth of a user of the device when measuring the flow rate of the air flow exhaled or inhaled by this user.

Preferably, the tubular mouthpiece presents a direction of extension coincident with the axis of revolution of the tubular conduit. The tubular mouthpiece presents orthogonal sections with respect to the circular and/or ovoid shaped axis of revolution.

According to another aspect of the disclosure, the tubular mouthpiece presents projections directed outwardly from the tubular mouthpiece. Each projection extends along a partial or full outer contour of the tubular mouthpiece, the contour belonging to a plane orthogonal to the axis of revolution.

According to one aspect of the disclosure, the tubular conduit presents a collar extending outwardly from the tubular conduit. Preferably, the collar is orthogonal to the axis of revolution.

According to one aspect of the disclosure, the tubular conduit, the structure, the tubular mouthpiece and the collar are integral with each other.

According to one aspect of the disclosure, the outer face comprises three surfaces, each arranged so as to serve as a bearing surface of a seal, the first surface and the second surface being arranged on either side of the second groove; the second surface and the third surface being arranged on either side of the first groove.

According to one aspect of the disclosure, the first surface is disposed at a first distance from the axis of revolution, the second surface is disposed at a second distance from the axis of revolution and the third surface is disposed at a third distance from the axis of revolution so that the first distance is smaller than the second distance and the second distance is smaller than the third distance.

Preferably, said surfaces are circular, each being arranged so as to serve as a bearing surface of a lip-type seal. This arrangement allows providing a location for measuring pressure in the first groove and in the second groove by affixing seals on said surfaces.

The arrangements allow for an easy insertion of a device according to the disclosure in a pressure measuring apparatus along an axis of insertion corresponding to the axis of revolution of the device, so as to cooperate with seals disposed in a coaxial and shifted manner along the axis of insertion, the seals presenting inner dimensions which decrease along the direction of insertion.

The present disclosure also concerns a system comprising a device, a pressure measuring apparatus arranged to measure simultaneously at least two pressures at two locations provided with connecting plugs, and at least one sealed connector provided between the apparatus and the device.

The sealed connector is fixed on the measuring apparatus so as to bring each groove into fluid communication with a defined connecting plug.

According to one aspect of the disclosure, the device and the measuring apparatus are secured to each other in a removable manner.

According to one aspect of the disclosure, the measuring apparatus comprises an opening for the introduction of the device in the measuring apparatus. The opening is arranged so that the device is introduced in the measuring apparatus along the axis of revolution, the second end of the device being the first to be introduced in the measuring apparatus.

According to another aspect of the disclosure, the collar presents a radial extent greater than the opening of the measuring apparatus. The collar is arranged to abut against the outer surface of the measuring apparatus. Said abutment is arranged for positioning the device relative to the measuring apparatus.

The first and second grooves of the device are inside the measuring apparatus when the device is secured to the measuring apparatus.

Preferably, the measuring apparatus comprises a snap-fitting system which cooperates with the collar of the device for securing the device to the measuring apparatus.

According to one aspect of the disclosure, the measuring apparatus comprises a spring plunger and a trigger arranged to actuate the snap-fitting system. When the snap-fitting system is handled by means of the trigger, the spring plunger, arranged to exert a force on the collar, disengages the device from the measuring apparatus and ejects the device out of the measuring apparatus.

This arrangement allows ejecting the device from the apparatus after use without having to intervene manually on the device. Thus, a second user does not touch the device previously used by a first user. Contamination between the first user and the second user or any other person handling the system is limited.

According to one aspect of the disclosure, three circular lip-type seals are brought on the inner wall of the opening of the measuring apparatus and are arranged to cooperate respectively with the first surface, the second surface and the third surface.

This arrangement allows establishing a sealed fluid communication, on the one hand, between the first groove and a first connecting plug, and on the other hand, between the second groove and a second connecting plug of the measuring apparatus.

The present disclosure also concerns a method for manufacturing a device by injection, wherein the material is injected during the same injection step.

BRIEF DESCRIPTION OF THE FIGURES

In any case, the disclosure will be better understood from the following description with reference to the appended schematic drawing representing, as a non-limiting example, an embodiment of this system and of this device.

DETAILED DESCRIPTION OF THE FIGURES

Figure 1:
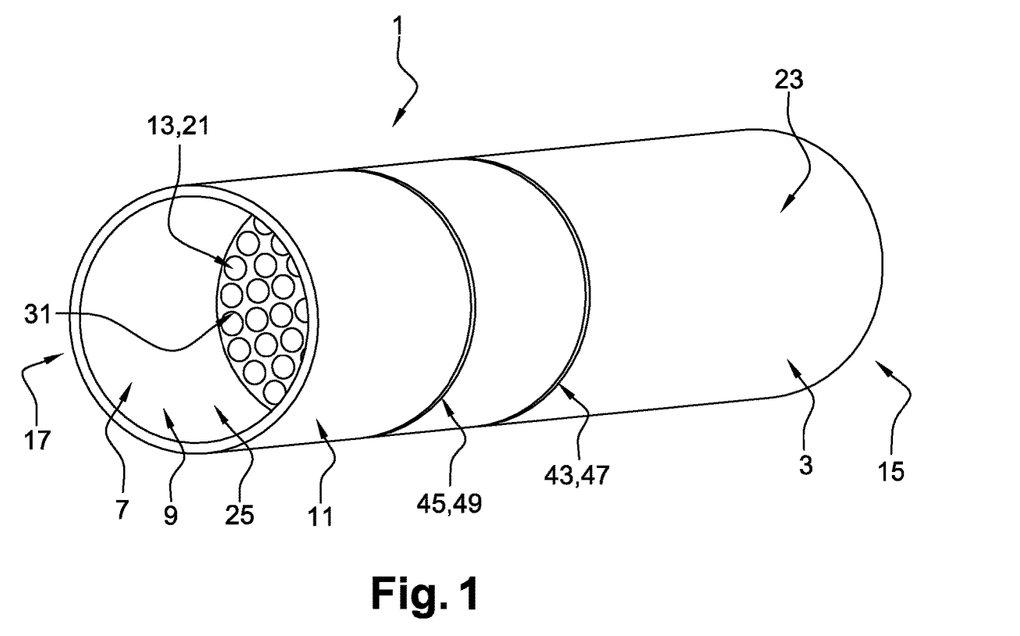
FIG. 1 is a perspective view of a device for measuring a flow rate of an air flow exhaled or inhaled by a person according to a first embodiment.
Figure 2:
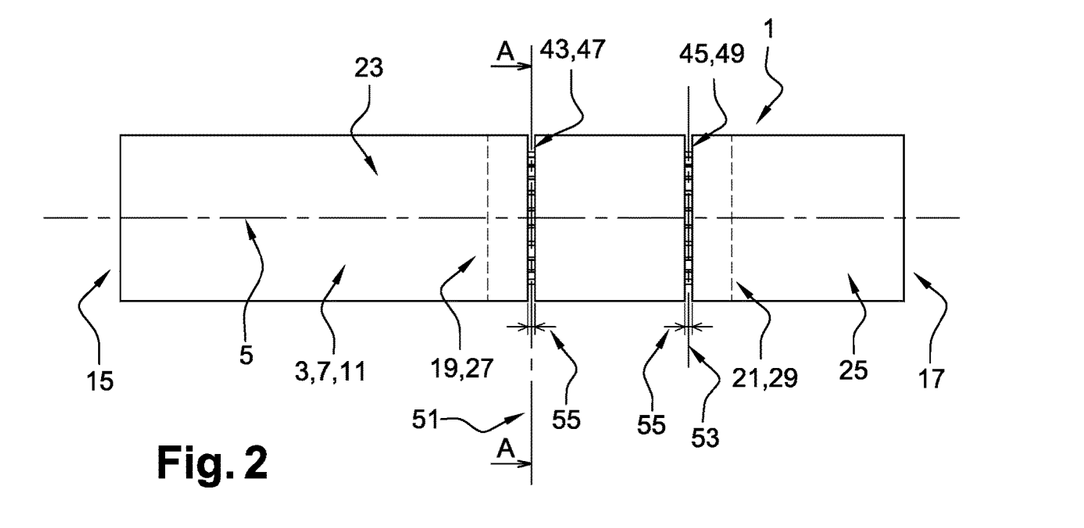
FIG. 2 is a front view of the device according to the first embodiment.

As illustrated in FIGS. 1 and 2, according to a first embodiment, a device 1, for measuring a flow rate of an air flow exhaled or inhaled by a person, comprises a tubular conduit 3. The tubular conduit 3 is a revolving conduit whose axis of revolution 5 is a straight line. The tubular conduit 3 is cylindrical and comprises a wall 7 presenting an inner face 9 and an outer face 11.

The device 1 also comprises a structure 13 disposed inside the tubular conduit 3 at a distance from a first end 15 and a second end 17 of the tubular conduit 3.

The structure 13 presents a first end 19 and a second end 21 along the direction of extension of the tubular conduit 3. A first free portion 23 of the tubular conduit 3 is located between the first end 15 of the tubular conduit 3 and the first end 19 of the structure 13. Similarly, a second free portion 25 is located between the second end 21 of the structure 13 and the second end 17 of the tubular conduit 3.

The first end 19 of the structure 13 is comprised in a first plane 27 transverse to the axis of revolution 5 and the second end 21 of the structure 13 is comprised in a second plane 29 transverse to the axis of revolution 5.

The structure 13 is secured to the inner face 9 of the wall 7 of the tubular conduit 3 and extends over the section of the tubular conduit 3 between the first end 19 and the second end 21 of the structure 13.

The structure 13 presents a plurality of channels 31 or capillaries extending parallel to the axis of revolution 5 of the tubular conduit 3 between the first end 19 of the structure 13 and the second end 21 of the structure 13. The plurality of channels 31 brings the inside of the first free portion 23 of the tubular conduit 3 into fluid communication with the inside of the second free portion 25 of the tubular conduit 3.

Figure 3:
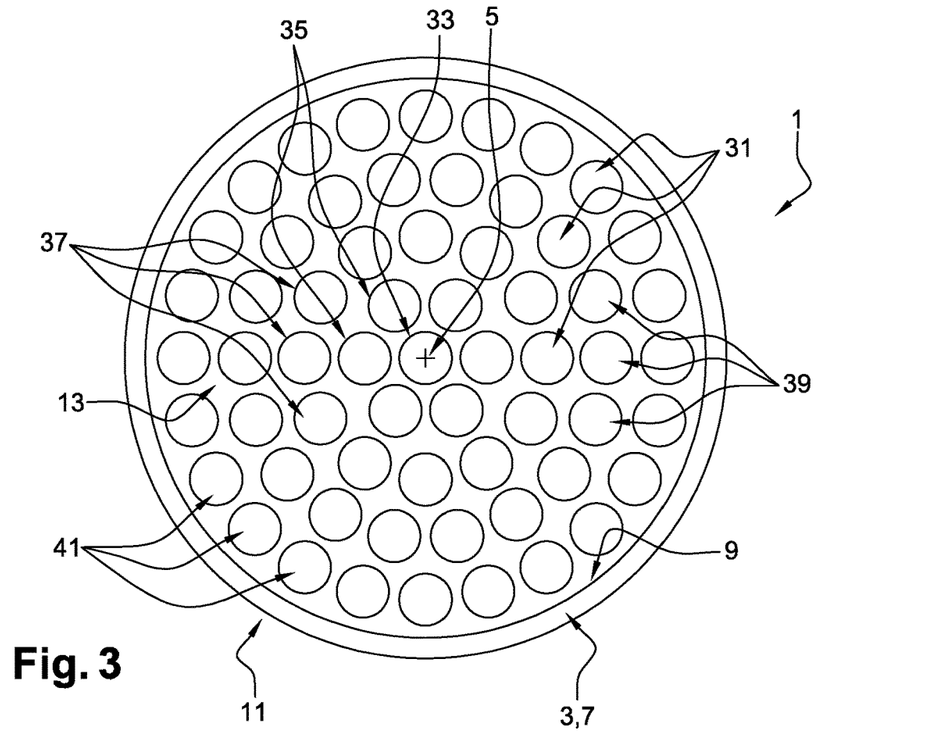
FIG. 3 is a side view of the device according to the first embodiment.

As illustrated in FIG. 3, the channels 31 present a circular section with an identical diameter. The channels 31 are evenly distributed around a central channel 33. The axis of extension of the central channel is coincident with the axis of revolution 5 of the tubular conduit 3.

A first group 35 of channels 31 surrounds the central channel 33, the axes of extension of the channels 31 of the first group 35 being equidistant from the axis of the central channel 33.

A second group 37 of channels 31 surrounds the channels of the first group 35, the axes of extension of the channels 31 of the second group 37 being equidistant from the axis of the central channel 33.

A third group 39 of channels 31 surrounds the channels of the second group 37, the axes of extension of the channels 31 of the third group 39 being equidistant from the axis of the central channel 33.

A fourth group 41 of channels 31 surrounds the channels of the third group 39, the axes of extension of the channels 31 of the fourth group 39 being equidistant from the axis of the central channel 33.

The radial distances with respect to the axis of revolution 5 of the tubular conduit 3, between the central channel 33 and the channels of the first group 35, are identical to the radial distances between the channels of the first 35 and second 37 groups, to the radial distances between the channels of the second 37 and third 39 groups, and to the radial distances between the channels of the third 39 and fourth 41 groups.

Each channel 31 belonging to a group 35, 37, 39, 41 is located at the same distance from the adjacent channels belonging to the same group 35, 37, 39, 41.

The channels 31 of the fourth group 41 constitute the peripheral channels 41 of the structure 13.

As illustrated in FIG. 2, the device 1 presents a first groove 43 and a second groove 45. Each groove 43, 45 opens onto the outer face 11 of the wall 7 of the tubular conduit 3 and is in fluid communication with the peripheral channels 41 of the structure 13. The second groove 45 is arranged at a distance from the first groove 43.

The first groove 43 extends along a first circumference 47 of the outer face 11 of the device 1, the first circumference 47 being comprised in a first plane 51 orthogonal to the axis of revolution 5 of the tubular conduit 3.

The second groove 45 extends along a second circumference 49 of the outer face 11 of the device 1, the second circumference 49 being comprised in a second plane 53 orthogonal to the axis of revolution 5 of the tubular conduit 3.

It should be noted that the first 51 and the second 53 orthogonal planes are located between the first 27 and the second 29 transverse planes. Thus, any flow circulating in a channel 31 is established between the first 51 and the second 53 orthogonal planes, that is to say that the flow presents a constant transverse profile of flow velocity with a non-turbulent flow regime over all sections of said channel between the first 51 and the second 53 orthogonal planes.

The first 43 and the second 45 grooves present an identical and constant width 55, the width 55 being the dimension of the grooves 43, 45 along the axis of revolution 5 of the tubular conduit 3.

Figure 4:
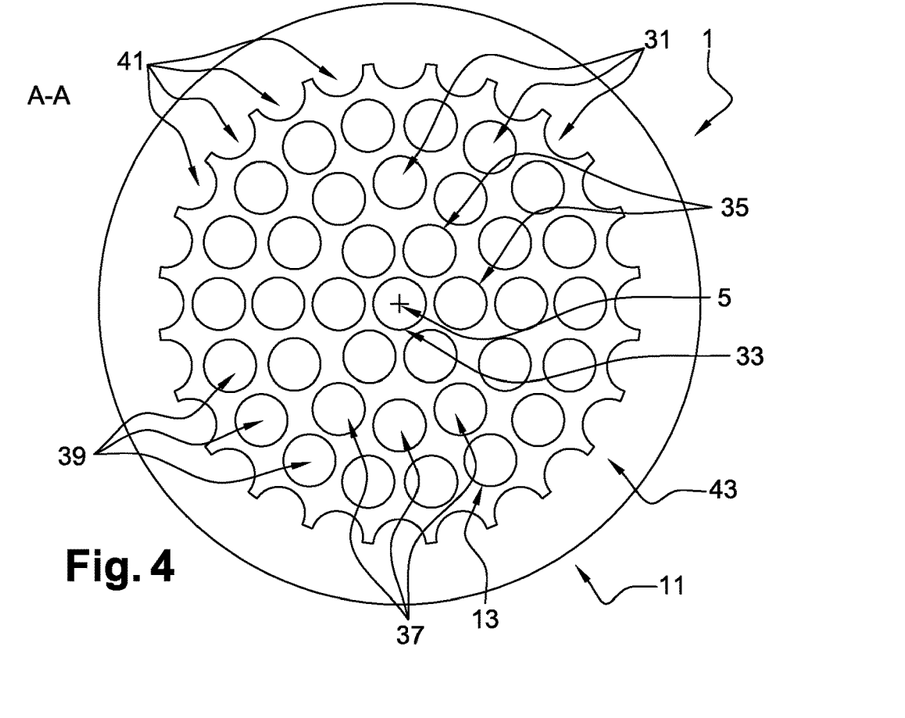
FIG. 4 is a cross-section of the device according to the first embodiment.

As illustrated in FIG. 4, a section A-A along the first orthogonal plane 51 shows the openings of the peripheral channels 41 at the level of the first groove 43.

As illustrated in FIGS. 5 to 10, according to a second and a third embodiments, the device 1 further comprises a collar 57. The collar 57 is brought on the outer face 11 of the tubular conduit 3 and extends along a direction orthogonal to the axis of revolution 5.

A tubular mouthpiece 59 is brought on the first end 15 of the tubular conduit 3 in a sealed manner. The tubular mouthpiece 59 presents a first end 61 with a section identical to the section of the first end 15 of the tubular conduit 3.

The tubular mouthpiece 59 presents projections 63 directed outwardly from the tubular mouthpiece 59. Each projection 63 extends along a full or partial outer contour of the tubular mouthpiece 59, the contour belonging to a plane orthogonal to the axis of revolution 5.

According to one aspect of the disclosure, the tubular conduit, the structure, the tubular mouthpiece and the collar are integral with each other and realized during the same injection step.

Figure 5:
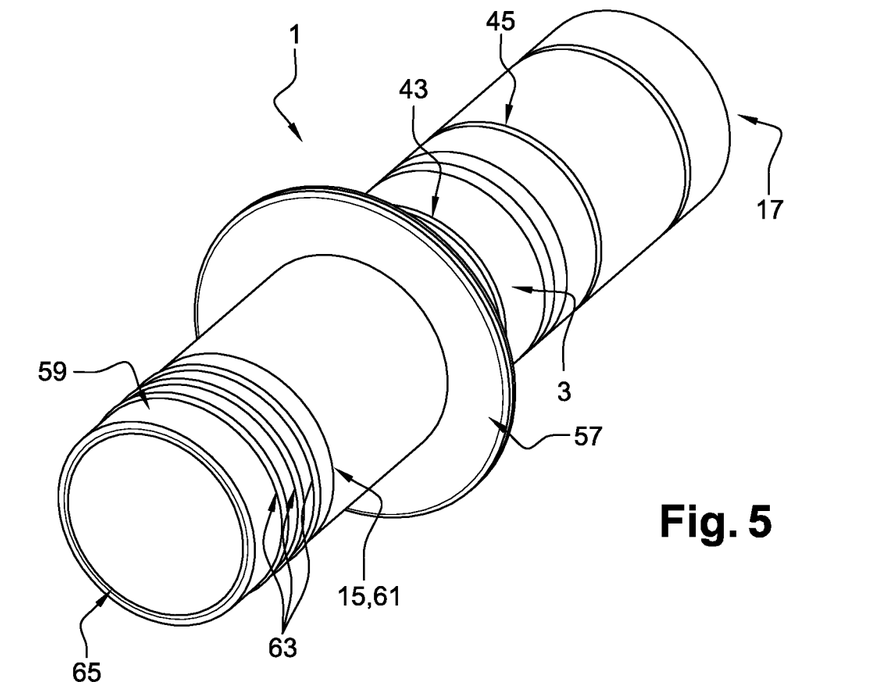
FIG. 5 is a perspective view of the device according to a second embodiment.
Figure 7:
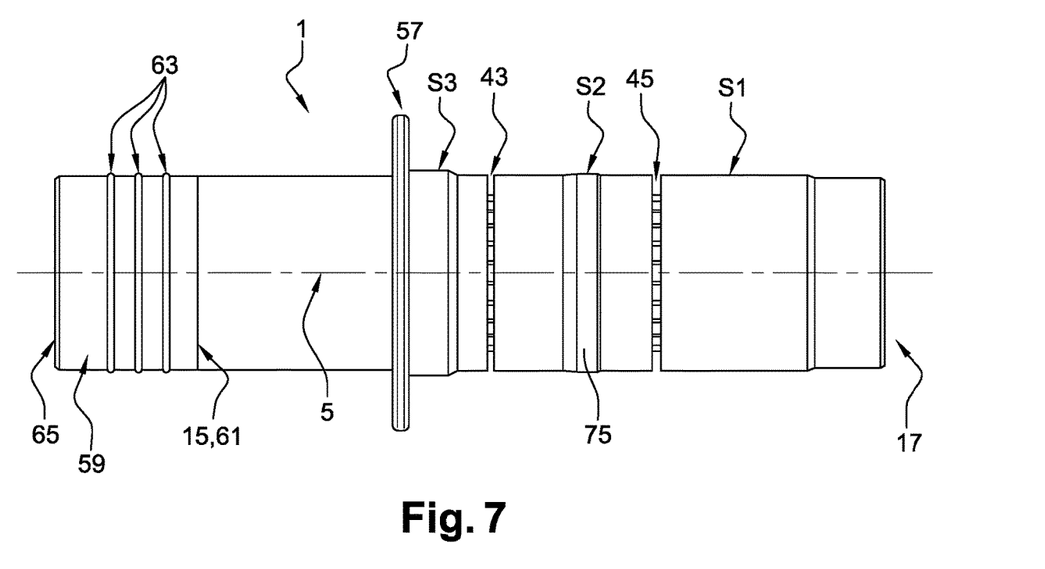
FIG. 7 is a front view of the device according to the second embodiment.
Figure 9:
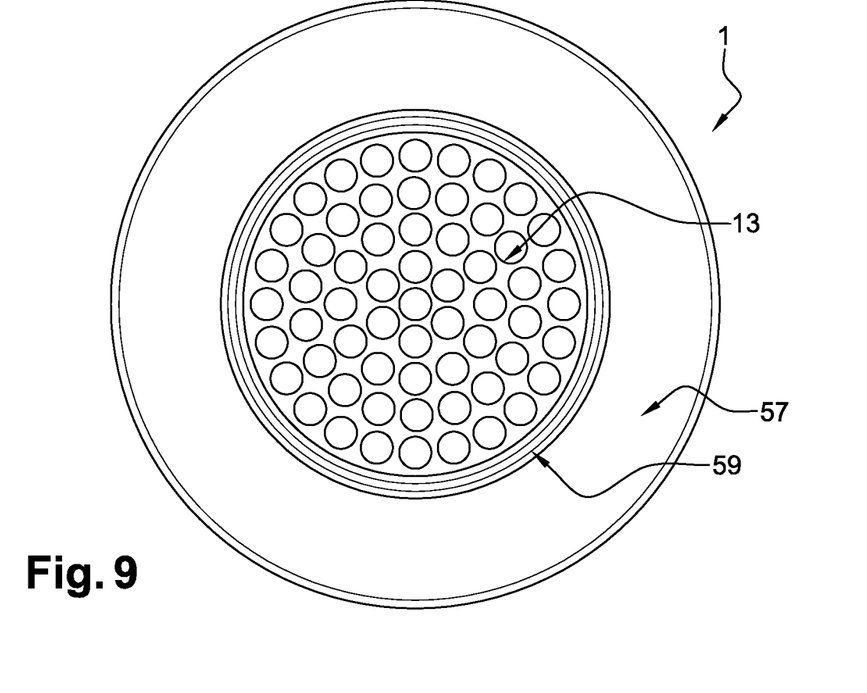
FIG. 9 is a side view of the device according to the second embodiment.

According to the second embodiment, illustrated in FIGS. 5, 7 and 9, the tubular mouthpiece 59 is a tube whose axis is the axis of revolution 5. Each projection 63 extends along a circumference of the tubular mouthpiece 59.

Figure 6:
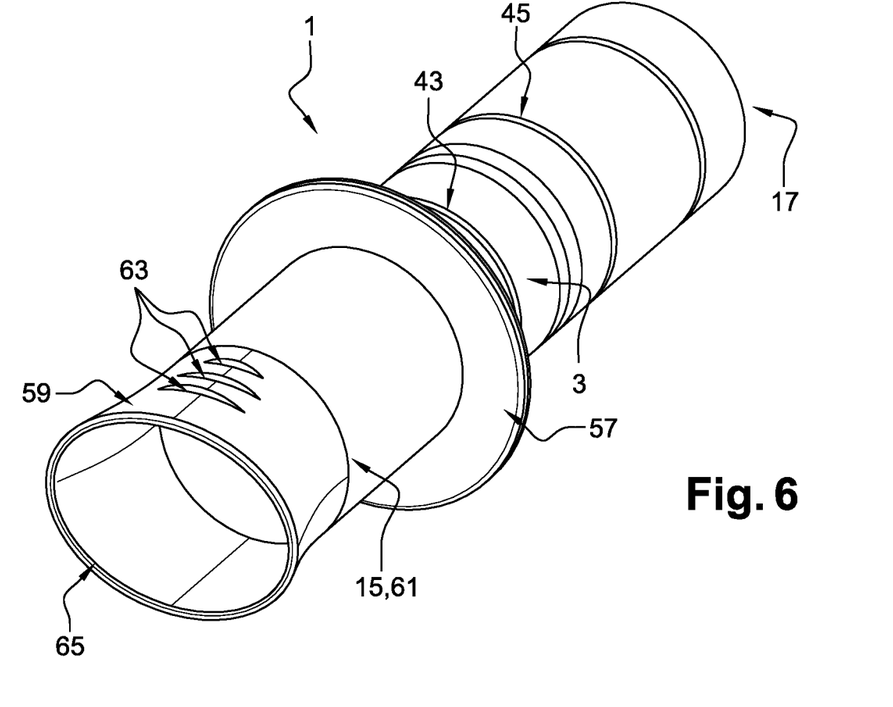
FIG. 6 is a perspective view of the device according to a third embodiment.
Figure 8:
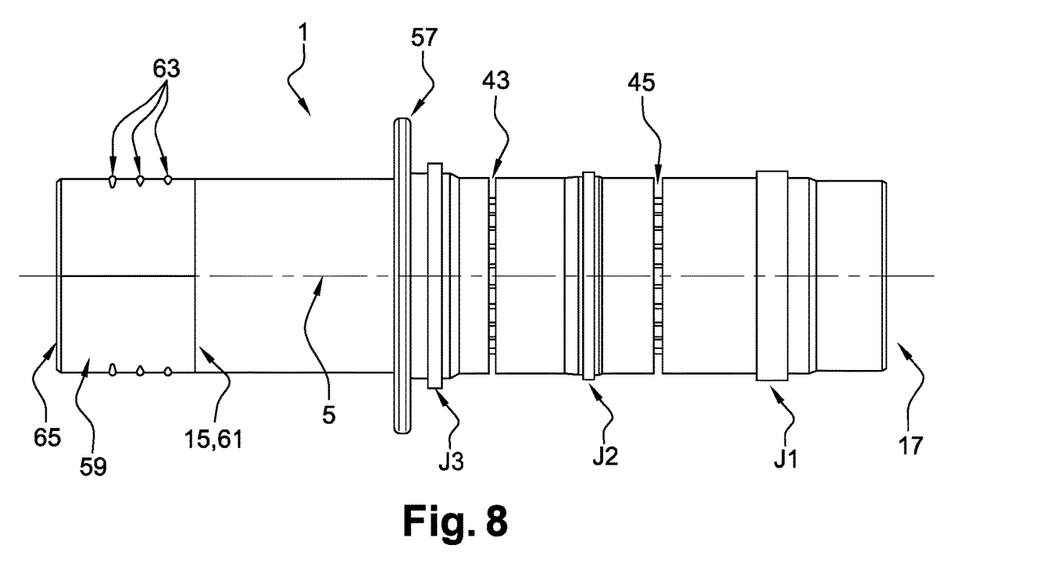
FIG. 8 is a front view of the device according to the third embodiment.
Figure 10:
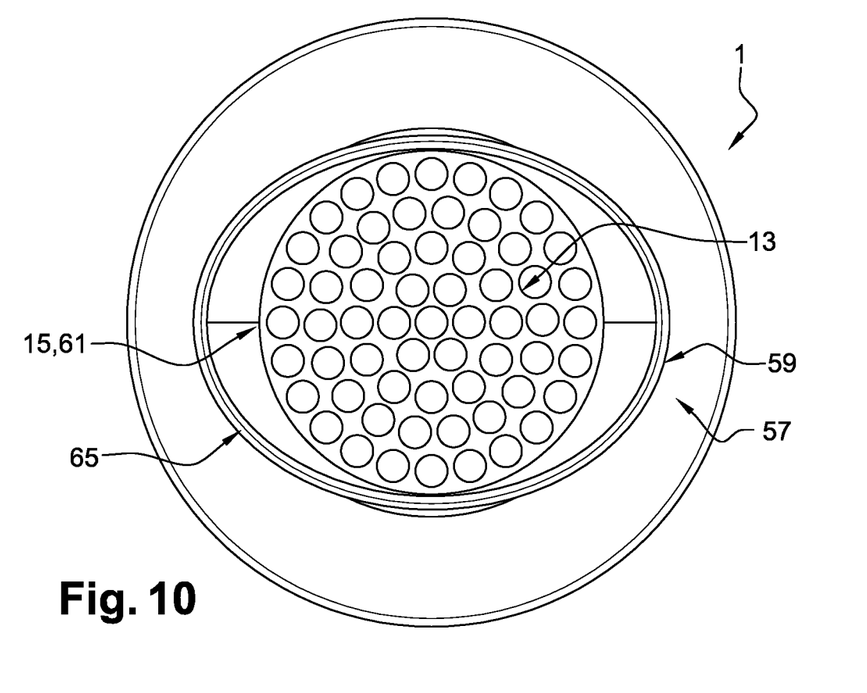
FIG. 10 is a side view of the device according to the third embodiment.

According to the third embodiment, illustrated in FIGS. 6, 8 and 10, the tubular mouthpiece 59 extends along the axis of revolution and presents a second end 65 with an ovoid section. The mouthpiece 61 presents a gradual change of section between the first end 61, with a circular section, and the second end 65, with an ovoid section. Each projection 63 extends along a portion of a circumference of the tubular mouthpiece 59 and is symmetrical to another projection 63 with respect to the point of intersection of the plane comprising said circumference and the axis of revolution 5.

Hereinabove, the device 1 for measuring an air flow rate has been described according to three embodiments.

The device 1 is comprised in a system 67 for measuring a flow rate of an air flow exhaled or inhaled by a person. It is to be understood that the person is considered to be the user of the device and of the system.

Figure 11:
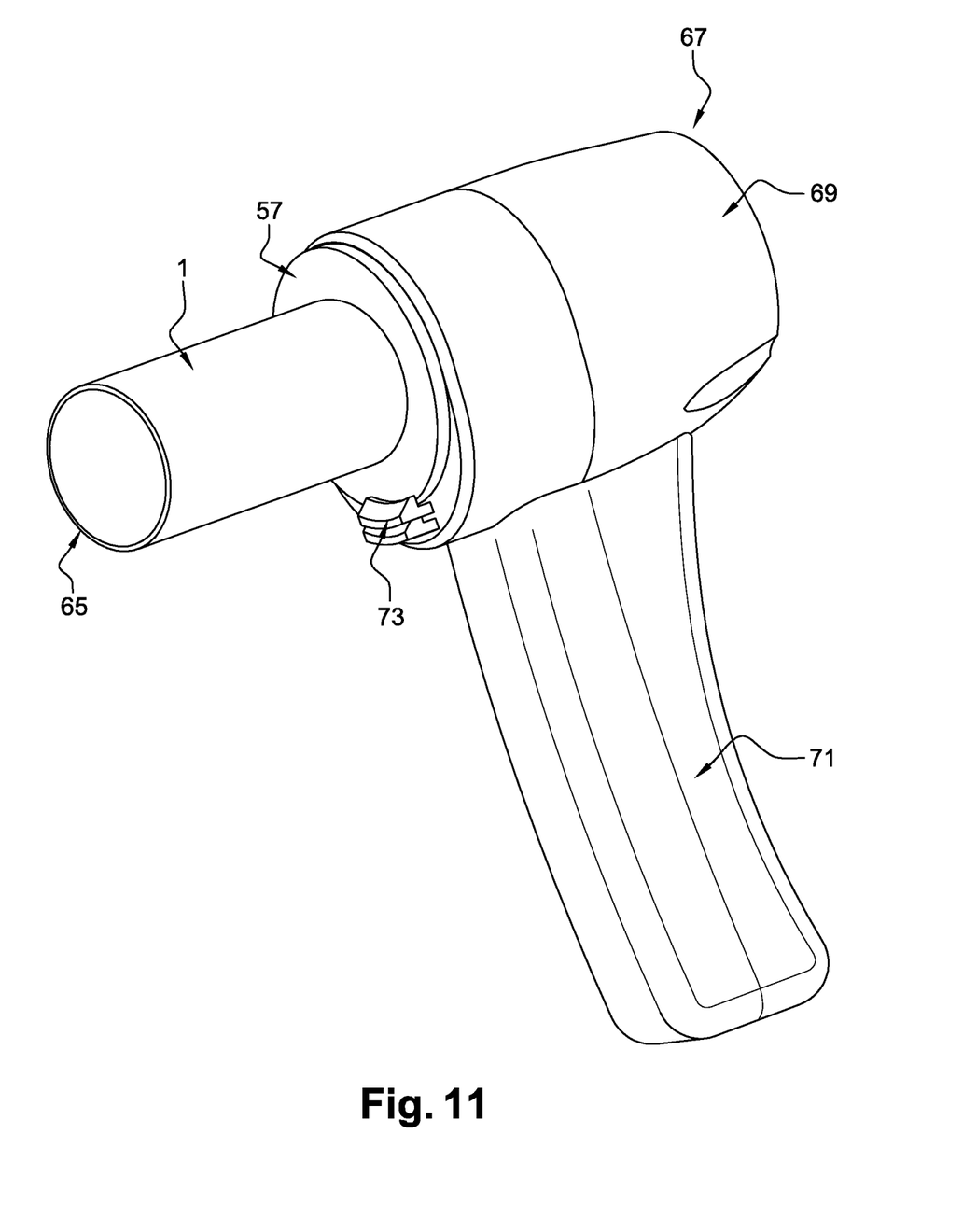
FIG. 11 is a view of a system comprising the device and a measuring apparatus according to the second embodiment.

As illustrated in FIG. 11, according to the second embodiment, the system 67 comprises a pressure measuring apparatus 69 arranged to simultaneously measure at least two pressures at two locations of the apparatus 69 which are provided with connecting plugs.

The apparatus comprises a gripping handle 71 arranged for positioning the first end of the device in the mouth of the user of the system 67.

The device 1 and the measuring apparatus 69 are secured to each other in a removable manner. For this purpose, the measuring apparatus 69 comprises an opening intended for introducing the device.

The device 1 is introduced in the measuring apparatus along the axis of revolution 5. The second end 17 of the device 1 being the first to be introduced in the measuring apparatus.

The collar 57 is arranged to abut against the outer surface of the measuring apparatus 69 for the positioning of the device 1 relative to the measuring apparatus 69.

The first 43 and the second 45 grooves of the device are inside the measuring apparatus 69 when the device 1 is secured to the measuring apparatus 69, as illustrated in FIG. 11.

The measuring apparatus 69 comprises a snap-fitting system 73 which cooperates with the collar 57 of the device 1 when securing the device 1 to the measuring apparatus 69.

According to one aspect of the disclosure, the measuring apparatus comprises a spring plunger and a trigger arranged to actuate the snap-fitting system 73. When the snap-fitting system 73 is handled by means of the trigger, the spring plunger, arranged to exert a force on the collar 57, disengages the device 1 from the measuring apparatus 69 and ejects the device 1 out of the measuring apparatus 69.

The system 67 also comprises sealed connectors between the measuring apparatus 69 and the device 1 so as to bring each groove 43, 45 of the device 1 into fluid communication with a connecting plug of the measuring apparatus 69.

As illustrated in FIGS. 7 and 8, the outer face 11 presents a circular section with different diameters between the collar 57 and the second end 17.

Starting from the first end 17 and towards the collar 57, the outer face 11 comprises a first circular surface S1 between the second end 17 and the second groove 45, a second circular surface S2 between the first groove 43 and the second groove 45, the second surface S2 being arranged atop a bead 75. The outer face 11 further comprises a third circular surface S3 arranged between the first groove 43 and the collar 57.

The section of the third surface S3 is larger than the section of the second surface S2, this section being in turn larger than the section of the first surface S1.

This arrangement allows introducing the device 1 in the measuring apparatus 69, as illustrated in FIG. 11.

The measuring apparatus 69 further comprises three circular lip-type seals respectively arranged to be carried by the surfaces S1, S2 and S3 (not represented in FIG. 11 because they are disposed inside the measuring apparatus 69). The seals disposed on the surfaces S3 and S2 ensure a sealed fluid communication between the first groove 43 and the connecting plug. The same applies for the seals disposed on the surfaces S2 and S1 for the second groove.

Thus, it appears that the insertion of the device 1 in the measuring apparatus 69 is easy and that the tightness of the pressure measurements is properly ensured by simply snap-fitting the device 1 in the measuring apparatus 69. After having described the constituent elements of the device 1 and of the measuring apparatus 69, the operation of the system 67 will be detailed hereinafter.

In a first step, the device 1 is inserted in the measuring apparatus 69 through the opening of the measuring apparatus 69. The device 1 is secured to the apparatus by the snap-fitting system 73.

In a second step, the user of the system inserts in his mouth the first end 15 of the tubular conduit 3, according to the first embodiment, or the second end 65 of the tubular mouthpiece 59, according to the second and third embodiments, so that the exhaled or inhaled flow passes entirely through the tubular conduit 3.

In a third step, the person inhales or exhales and the differential pressure between the first 43 and the second 45 grooves is simultaneously measured with the measuring apparatus.

In a fourth step, the inhaled or exhaled flow rate is determined from the differential pressure. Indeed, the flows in the channels are Poiseuille flows. Thus, it is possible to obtain the flow rate of the air flow because, for this type of flow, the flow rate is related to the differential pressure, to the section of the channels 31 and to the distance between the first 51 and the second 53 orthogonal planes.

It goes without saying that the disclosure is not limited to the sole embodiment of this system and of this device, which has been described above as an example, but it encompasses, on the contrary, all variants thereof.

The invention claimed is:

1. A system comprising:
   a device for measuring a flow rate of an air flow exhaled or inhaled by a person, comprising:
      a tubular conduit provided for conducting said air flow, the tubular conduit comprising a wall presenting an inner face and an outer face, a revolving conduit, an axis of revolution of the revolving conduit being coincident with the direction of extension of the tubular conduit, and
      a structure disposed in the tubular conduit and having a plurality of channels configured for dividing the air flow;
   wherein the device further includes:
      a first groove made within the outer face and opening onto the outer face of the wall of the tubular conduit and being in fluid communication with at least one peripheral channel of the structure, and
      a second groove made within the outer face and opening onto the outer face of the wall of the tubular conduit and being in fluid communication with said at least one peripheral channel, the second groove being arranged at a distance from the first groove wherein the tubular conduit and the structure are made in one piece, a pressure measuring apparatus simultaneously measuring at least two pressures at two locations, the device for measuring a flow rate being snap-fitted in the pressure measuring apparatus according to an axis of insertion corresponding to the axis of the device for measuring a flow rate, the pressure measuring apparatus being provided with connecting plugs, and at least one sealed connector including three lip seals provided between the apparatus and the device, the sealed connector being fixed on the measuring apparatus and bringing each groove into fluid communication with a defined connecting plug of the apparatus, wherein the outer face of the tubular conduit comprises a first surface, a second surface, and a third surface, each of the surfaces being a bearing surface cooperating with a corresponding lip seal, the first surface and the second surface being arranged on either side of the second groove; the second surface and the third surface being arranged on either side of the first groove, the lip seals disposed on the second and third surfaces ensuring a sealed fluid communication between the first groove and a corresponding connecting plug, and, the lip seals disposed on the first and second surfaces ensuring a sealed fluid communication between the second groove and another corresponding connecting plug, and wherein the first surface is disposed at a first distance from the axis of revolution, the second surface is disposed at a second distance from the axis of revolution and the third surface is disposed at a third distance from the axis of revolution wherein the first distance is smaller than the second distance, and the second distance is smaller than the third distance, the three lip seals of the pressure measuring apparatus being disposed in a coaxial and shifted manner along the axis of insertion, the three lip seals presenting inner dimensions which decrease along the direction of insertion.

2. The system according to claim 1, wherein the first groove is in fluid communication with a plurality of peripheral channels of the structure, and wherein the second groove is in fluid communication with said plurality of peripheral channels of the structure.

3. The system according to claim 2, wherein the first groove extends along a first circumference of the outer face of the tubular conduit and the second groove extends along a second circumference of the tubular conduit.

4. The system according to claim 1, wherein the structure extends over a section of the tubular conduit.

5. The system according to claim 1, wherein the first and the second grooves are at a distance from the ends of the peripheral channels.

6. The system according to claim 1, wherein the first circumference is comprised in a first plane orthogonal to the axis of revolution and wherein the second circumference is comprised in a second plane orthogonal to the axis of revolution.

7. The system according to claim 1, wherein the channels present identical sections, in every plane orthogonal to the axis of revolution between the ends of the channels except the planes passing through the first groove and the planes passing through the second groove.

8. The system according to claim 7, wherein the channels are evenly distributed around a central channel.

9. The system according to claim 1, wherein the tubular conduit is a straight tube.

10. A method for manufacturing a device of the system according to claim 1, by injection, wherein the injection is realized in a single injection step.

* * * * *